(12) United States Patent
Kohné et al.

(10) Patent No.: US 6,817,483 B2
(45) Date of Patent: Nov. 16, 2004

(54) DIAPER DISPENSER

(75) Inventors: Michael Kohné, Am Eichberg 6, Glottertal (DE), 79286; Martina Finken, Auxon les Vesoul (FR)

(73) Assignee: Michael Kohne, Glottertal (DE)

( * ) Notice: Subject to any disclaimer, the term of this patent is extended or adjusted under 35 U.S.C. 154(b) by 39 days.

(21) Appl. No.: 10/316,848

(22) Filed: Dec. 12, 2002

(65) Prior Publication Data

US 2003/0111485 A1 Jun. 19, 2003

(30) Foreign Application Priority Data

Dec. 14, 2001 (DE) .......................... 101 61 617

(51) Int. Cl.[7] .............................................. A47K 10/24
(52) U.S. Cl. .......................................... 221/45; 206/494
(58) Field of Search ........................ 221/33, 34, 44–48, 221/55, 56, 63, 281, 304; 206/494, 248, 449

(56) References Cited

U.S. PATENT DOCUMENTS

| | | | |
|---|---|---|---|
| 2,923,435 A | * | 2/1960 | Chaplin ........................ 221/47 |
| 3,156,378 A | | 11/1964 | Bua |
| 4,491,242 A | | 1/1985 | Trinidad |
| 4,573,608 A | | 3/1986 | Hansen |
| 4,706,845 A | | 11/1987 | Schnurer et al. |

FOREIGN PATENT DOCUMENTS

| | | |
|---|---|---|
| CA | 2 156 307 A1 | 2/1997 |
| DE | 36 21 550 A1 | 1/1988 |
| DE | 296 07 763 | 9/1996 |
| FR | 2 773 315 A1 | 7/1999 |
| GB | 402 802 A | 12/1933 |
| GB | 1 180 434 A | 2/1970 |

* cited by examiner

*Primary Examiner*—Kenneth Noland
(74) *Attorney, Agent, or Firm*—Edell, Shapiro & Finnan, LLC

(57) ABSTRACT

A diaper dispenser simplifying the storage and removal of diapers consists of a container (1) designed for receiving horizontally stacked diapers, comprising a front wall (2), a bottom (9), and a removal opening (7, 8) disposed therebetween. The removal opening includes an approximately slot-shaped entry hole extending upwards from the lower edge (2c) of the front wall (2), preferably for the thumb of the hand, and a recess defined by a set-off of the edge (9a) of the bottom (9) on the side of the front wall, so that the respective bottommost diaper preferably comes to lie between thumb and index finger of the removing hand and can be withdrawn at an angle in forward and downward direction.

10 Claims, 3 Drawing Sheets

DIAPER DISPENSER

BACKGROUND OF THE INVENTION

1. Field of the Invention

This invention relates to a diaper dispenser consisting of a container designed for receiving horizontally stacked diapers, comprising a wall, a bottom and a removal opening disposed therebetween, through which the bottommost diaper can be withdrawn.

2. Description of the Related Art

Ready-made diapers intended for single usage, so-called disposable diapers, are put on the market rectangularly folded and packed individually in stacks of, for instance, 50 piece. Cotton diaper cloths usually likewise are kept ready for usage folded to an approximately rectangular format and stacked. The diaper stacks generally deposited on the changing table can easily tip over in particular when removing a diaper.

This is avoided by a diaper dispenser of the type mentioned above, which is designed for receiving disposable diapers and is known from DE 296 07 763 U. The removal opening constitutes a transverse slot at the bottom end of one of the two side walls of the container and is defined below by the corresponding edge of the container bottom having a small recess and above by the lower edge of the correspondingly shortened side wall. The side wall also has a longitudinal slot opening into the transverse slot for checking the filling level. This construction for removing the respective bottommost diaper is not much practicable.

A diaper dispenser of quite similar design with the same disadvantages, which in addition must be charged with the diapers from above, is known from DE 296 21 781 U.

Another diaper dispenser is known from DE 201 03 529 U1. In these diaper dispensers, too, the diapers must be charged from above, which in the case of a diaper stack comprising e.g. 50 diapers involves the risk that the stack will fall apart, so that one or more diapers no longer lie flat, but are jammed or bent. As a result, both the removal of the diapers and the proper descent of the stack after each removal is made more difficult or even blocked. Removal is effected through an opening disposed in the container wall and thus aligned horizontally, supported by an inclined intermediate bottom as additional part, which requires a separate attachment.

SUMMARY OF THE INVENTION

It is the object underlying the invention to create a diaper dispenser which simplifies the storage and removal of the diapers.

In accordance with the invention, this object is solved by a diaper dispenser with the features indicated in claim 1.

The container forming the diaper dispenser has an inner cross-section adapted to the very similar format of folded disposable diapers also of different manufacturers. Normally, conventional cotton diaper cloths are also folded to the same format. The height of the container can be dimensioned such that it can receive two commercially available packaging units of e.g. 50 piece disposable diapers stacked one above the other. The container can have feet or a pedestal, so that its removal opening is accessible from below. However, the container primarily is designed for attachment to a wall. This has the advantage that the space requirement for keeping ready the diapers on the changing table is eliminated or at least reduced. The most important advantage of the diaper dispenser, however, consists in that the respective bottommost diaper can directly be withdrawn from the diaper dispenser in forward and downward direction in no time at all.

The removal opening on the one hand comprises an entry hole, and on the other hand a recess in the bottom of the container which extends at least almost across the entire container width. The entry hole preferably is arranged centrally at the lower edge of the front wall of the container and is optimally designed for entry with the thumb, so that the fingers come to lie below the bottommost diaper in the vicinity of the bottom recess. The flute in the vicinity of the entry hole ensures that the bottom diapers are slightly upset in the direction towards the rear wall of the container and the bottommost diaper can better be seized between thumb and fingers.

The entry hole preferably has a height exceeding the thickness of a stacked diaper (claim 2). However, its height expediently is distinctly smaller than twice the thickness of a stacked diaper (claim 3), so that the entering thumb separates the bottommost diaper from the second bottommost diaper automatically, so to speak, and said bottommost diaper then can be withdrawn in downward direction through the recess in the bottom of the container by applying a slight pressure.

The fact that the stock of diapers is running short can easily be recognized when the front wall has inspection windows (claim 4). One inspection window can be enough. Instead, there can be arranged a plurality of inspection windows at different levels or one elongate inspection window.

Expediently, the container approximately has the shape of a straight, tetrahedral prism (claim 5), which for design reasons can have slightly rounded shapes.

To adapt its inner cross-section to diaper stacks of different formats, the container preferably has an inner wall which can be adjusted and fixed parallel to the rear wall of the container in the direction towards the front wall (claim 6).

Fixing the inner wall can be achieved in particular by an elastic design and the cooperation of ribs in the container bottom and in the container cover surface or in the container side walls, which ribs are parallel to the rear wall of the container, and corresponding detents on the corresponding edges of the inner wall.

To ensure that the folded diapers remain lying flat in the stack moving downwards and reducing its height with each removal of a diaper, weighting the stack of diapers by a plate-shaped body or the like can be expedient (claim 7).

Advantageously, at least one of the container side walls can be designed for attachment of a deposition bracket (claim 8), on which e.g. powder or cream receptacles can be deposited.

In the drawing, the diaper dispenser in accordance with the invention is represented in an embodiment chosen by way of example, simplified in part, in which:

DETAILED DESCRIPTION OF THE INVENTION

Figure 1:
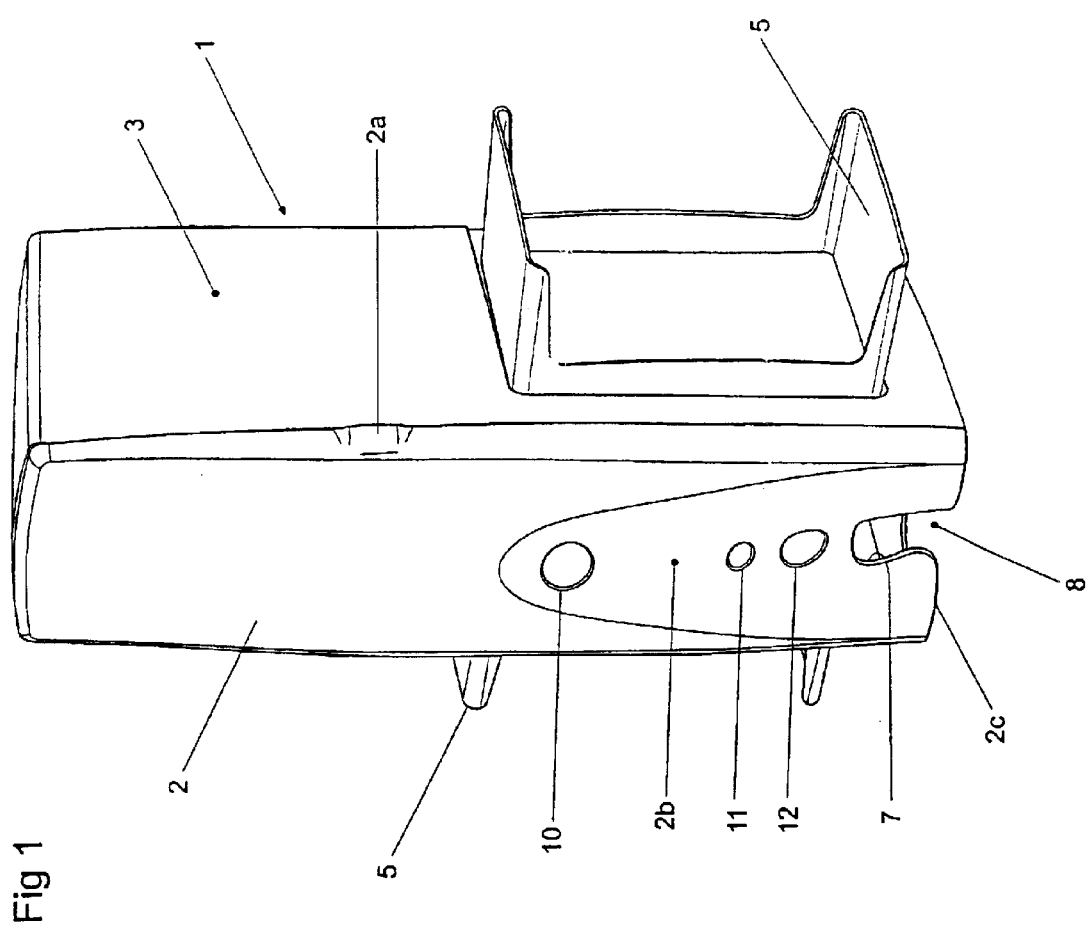
FIG. 1 shows a perspective view.
Figure 2:
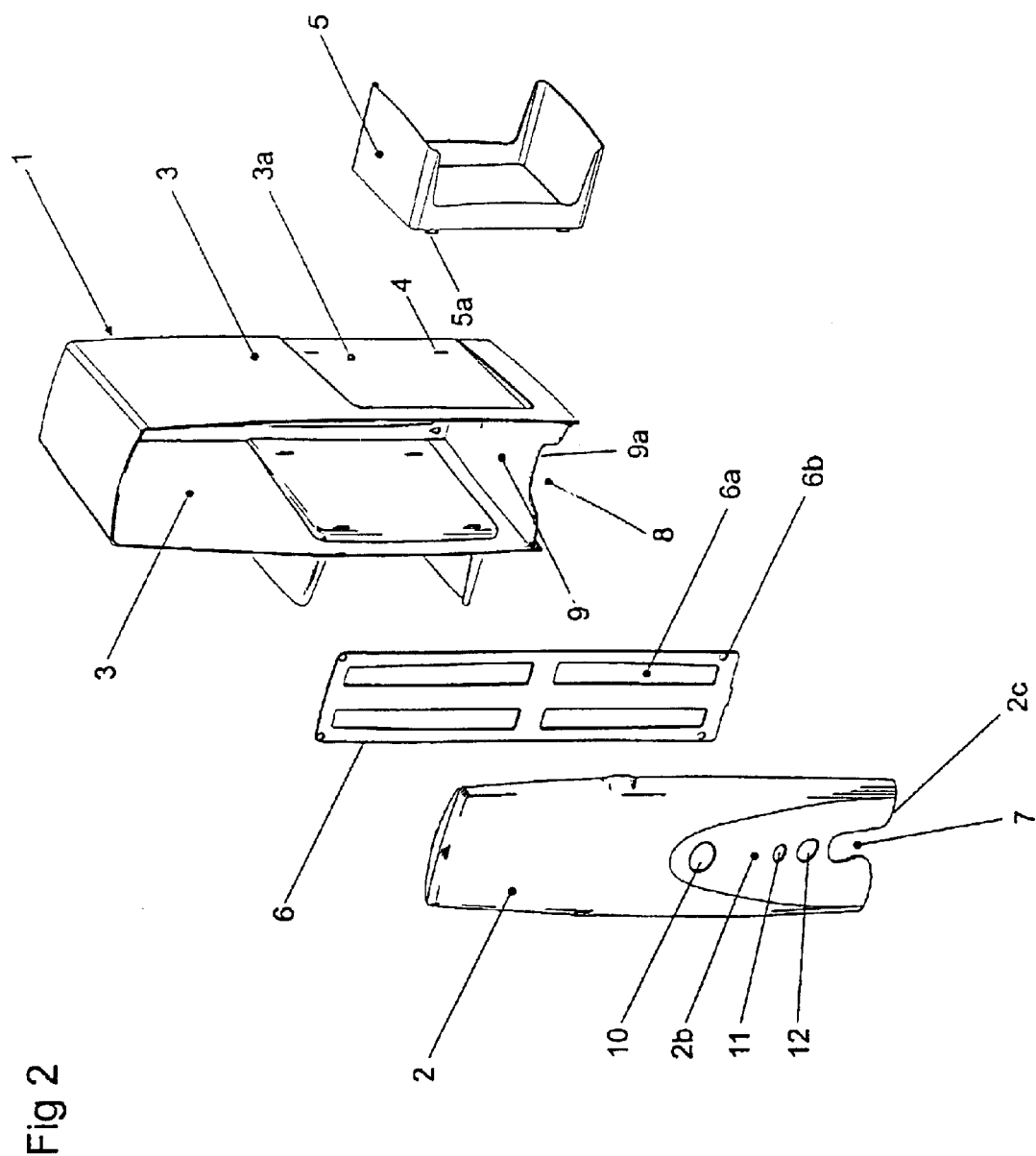
FIG. 2 shows an exploded representation.
Figure 3:
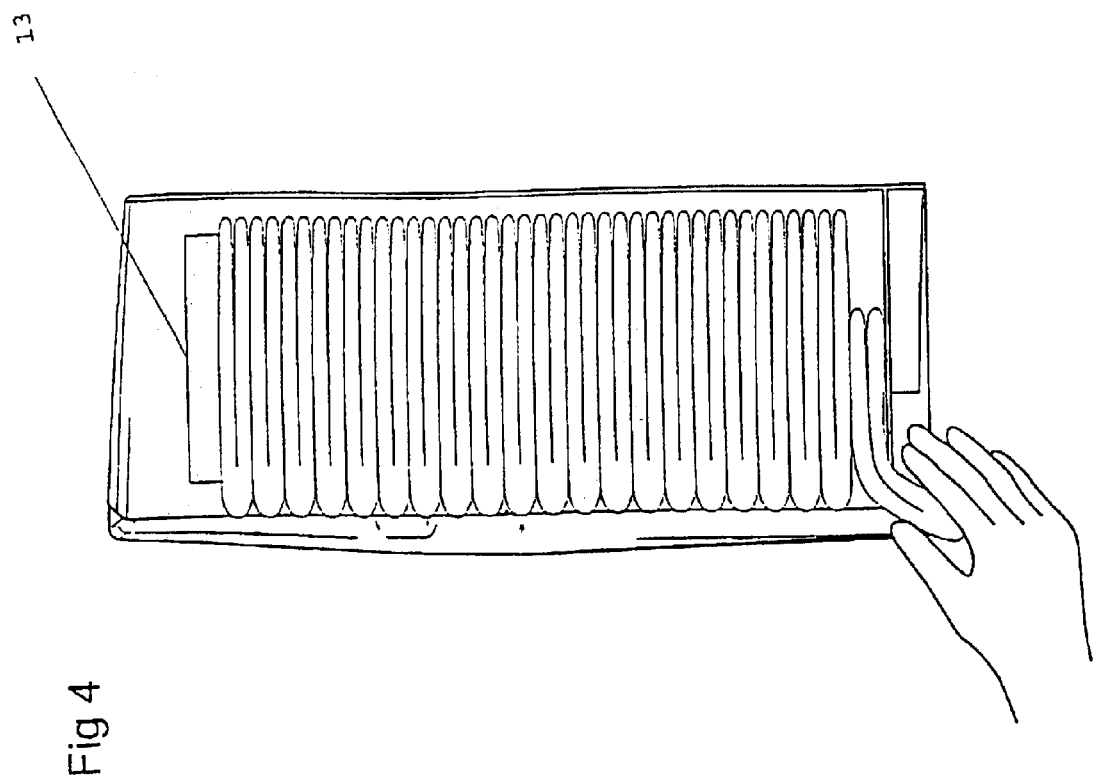
FIGS. 3 and 4 show schematic side views of the filled container to illustrate the removal.

The diaper dispenser represented in FIGS. 1 and 2 comprises an approximately parallelepiped container 1, preferably in the form of a deep-drawn plastic part, with internal dimensions for receiving for instance a stack of disposable diapers folded once (cf. e.g. FIG. 3). The container has a front wall which constitutes a cover 2 to be snapped onto the container 1 via detents such as 2a in FIG. 1. The container side walls 3 have recessed plane faces 3a with slots 4 for hanging in lateral brackets 5 formed with corresponding hooks 5a.

The container 1 includes an inner wall 6 which can be adjusted and fixed parallel to the rear wall of the container in the direction towards the cover 2, in order to be able to adapt the inner cross-section of the container 1 to stacks of diapers whose format is smaller than the maximum format predetermined by the depth of the container. For saving weight and material, the inner wall 6 merely has four longitudinal slots 6a as well as four holes 6b through which not represented congruent holes in the container rear wall are accessible, which are intended to receive screws by means of which the container 1 can be attached to a wall. For fixing the inner wall 6, the container can have ribs at suitable points, in which ribs the edges of the inner wall 6 snap in elastically.

The cover 2 has a trough-like flute 2b proceeding from its lower edge, which runs out at half the height of the cover 2. In this region, a depression 10, which can serve to attach a trademark, and two windows 11 and 12 are disposed from the top to the bottom. These windows can be simple holes or transparent plastic discs. They provide for checking the filling level and thus are superfluous when the container 1 or at least the cover 2 are made of an at least translucent plastic material.

What is particularly important for the functionality is the design of the removal opening for the diapers. The removal opening comprises two cooperating recesses, namely on the one hand an entry hole 7, which in the form of a central slot extends from the lower edge 2c of the cover 2 up to a height which is slightly greater than the thickness of an average folded diaper. The entry hole 7, which is disposed in the deepest region of the trough-like flute 2b, is ergonomically shaped such that it is quite obvious for the user to introduce the thumb of his right or left hand. As shown in FIG. 3, the fingers then come to lie below the bottommost diaper in a recess 8 forming the second part of the removal opening, which recess is formed in the bottom 9 of the container 1 as set-off of its edge 9a on the side of the front wall. The set-off extends from side wall 3 to side wall 3, expediently, but not necessarily, such that in the middle, at the level of the entry hole 7, it has its greatest depth or opening width. Its minimum depth and thus the minimum width of the recess 8 in the bottom 9 of the container 1 must, however, be approximately equal to the thickness of the thickest commercially available diaper or diaper to be removed from the container.

Figure 4:
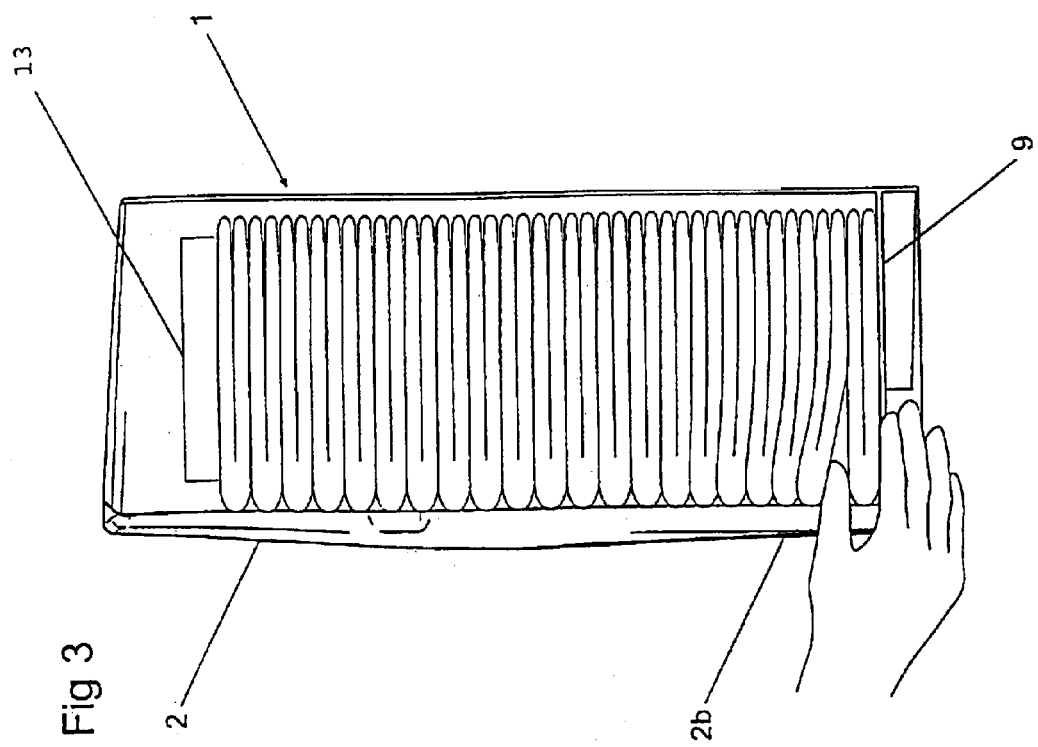

FIGS. 3 and 4 illustrate the removal procedure. The thumb introduced through the entry hole separates the bottommost diaper from the second bottommost diaper. The bottommost diaper is seized between thumb and the fingers, slightly tilted downwards in the seized region, and then withdrawn at an angle in forward/downward direction through the slot-shaped recess in the bottom 9 of the container 1. A weighting plate 13 ensures that the stack of diapers descends reliably, the diapers maintaining their flat position.

What is claimed is:

1. A diaper dispenser for receiving horizontally stacked diapers, comprising:

a front wall that is removable from the diaper dispenser, the front wall including a flute originating from a lower edge of the front wall and extending longitudinally along the front wall; and a bottom, wherein a removal opening is disposed between the front wall and the bottom through which a bottommost diaper can be withdrawn, the removal opening comprising an approximately slot-shaped entry hole extending upwards from the lower edge of the front wall within the flute and a recess comprising a set-off of a front edge of the bottom from the lower edge of the front wall.

2. The diaper dispenser as claimed in claim 1, wherein the entry hole has a height exceeding a thickness of a stacked diaper.

3. The diaper dispenser as claimed in claim 1, wherein the entry hole has a height smaller than twice a thickness of a stacked diaper.

4. The diaper dispenser as claimed in claim 1, wherein the front wall has at least one inspection window.

5. The diaper dispenser as claimed in claim 1, wherein the diaper dispenser approximately has the shape of a straight, tetrahedral prism.

6. The diaper dispenser as claimed in claim 1, wherein for adapting an inner cross-section to diaper stacks of different formats the diaper dispenser has an inner wall which can be adjusted and fixed parallel to a rear wall of the diaper dispenser in a direction towards the front wall.

7. The diaper dispenser as claimed in claim 1, further comprising a plate-shaped body for weighting the stacked diapers.

8. The diaper dispenser as claimed in claim 1, further comprising first and second side walls and a deposition bracket attached to at least one of the first and second side walls.

9. The diaper dispenser as claimed in claim 1, further comprising first and second side walls, wherein said front wall is substantially equal in length to the first and second side walls.

10. The diaper dispenser as claimed in claim 1, wherein the front wall snaps onto the diaper dispenser.

* * * * *